United States Patent [19]

Zadini et al.

[11] Patent Number: 5,579,780
[45] Date of Patent: Dec. 3, 1996

[54] MANUAL GUIDEWIRE PLACEMENT DEVICE

[76] Inventors: Filiberto P. Zadini, 16814 Rayen St., North Hills, Calif. 91343; Giorgio C. Zadini, 2237 Hilltop La., Camarillo, Calif. 93012

[21] Appl. No.: 321,554

[22] Filed: Oct. 11, 1994

[51] Int. Cl.$^6$ ............................................. A61B 5/00
[52] U.S. Cl. .................................. 128/772; 604/168
[58] Field of Search ............................. 128/657, 772; 604/95, 158, 159, 164, 168, 272

[56] References Cited

U.S. PATENT DOCUMENTS

| | | | |
|---|---|---|---|
| 4,274,408 | 6/1981 | Nimrod | 604/168 |
| 4,317,445 | 3/1982 | Robinson | 604/168 |
| 4,655,750 | 4/1987 | Vaillancourt | 604/168 |
| 4,874,376 | 10/1989 | Hawkins | 128/772 |
| 5,306,254 | 4/1994 | Nash et al. | 128/772 |

*Primary Examiner*—Max Hindenburg

[57] ABSTRACT

An improved manual guidewire placement device to facilitate successful guidewire placement into a blood vessel by minimizing risks of needle tip disengagement with a penetrated blood vessel and by minimizing risks of blood vessels overpenetration.

The device comprises a needle, a guidewire slideable within the needle, means of manually creating vacuum to accelerate backflow of blood upon occurred blood vessel penetration, means for manually advancing the guidewire, said means for manually advancing the guidewire being actuated by said means for creating the vacuum.

Actuation of said means for guidewire advancement may be either achieved by release of said means for guidewire advancement, said advancing means being positioned within easy reach of the operator's hand which creates the vacuum, so that no repositioning of the vacuum creating hand nor a two hands operation is required, or may be accomplished by conversion of the manual action exerted upon said vacuum creating means into a guidewire advancing action exerted upon said means for advancing the guidewire. The above features are aimed at minimizing loss of needle tip engagement within the blood vessel and at preventing overpenetration.

18 Claims, 8 Drawing Sheets

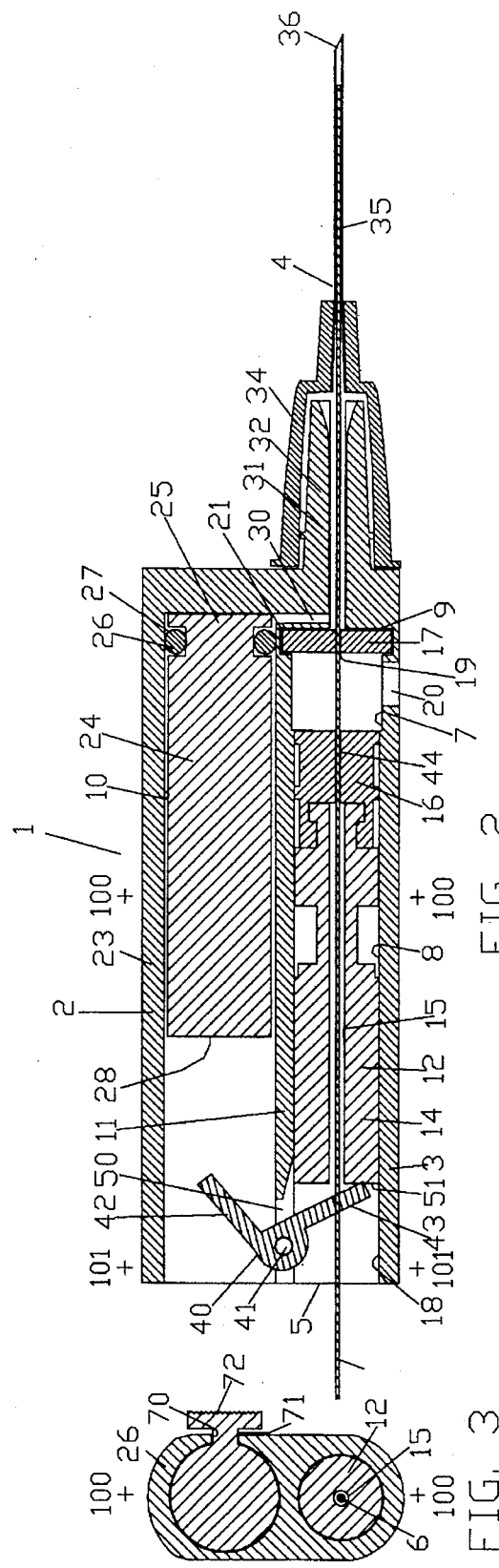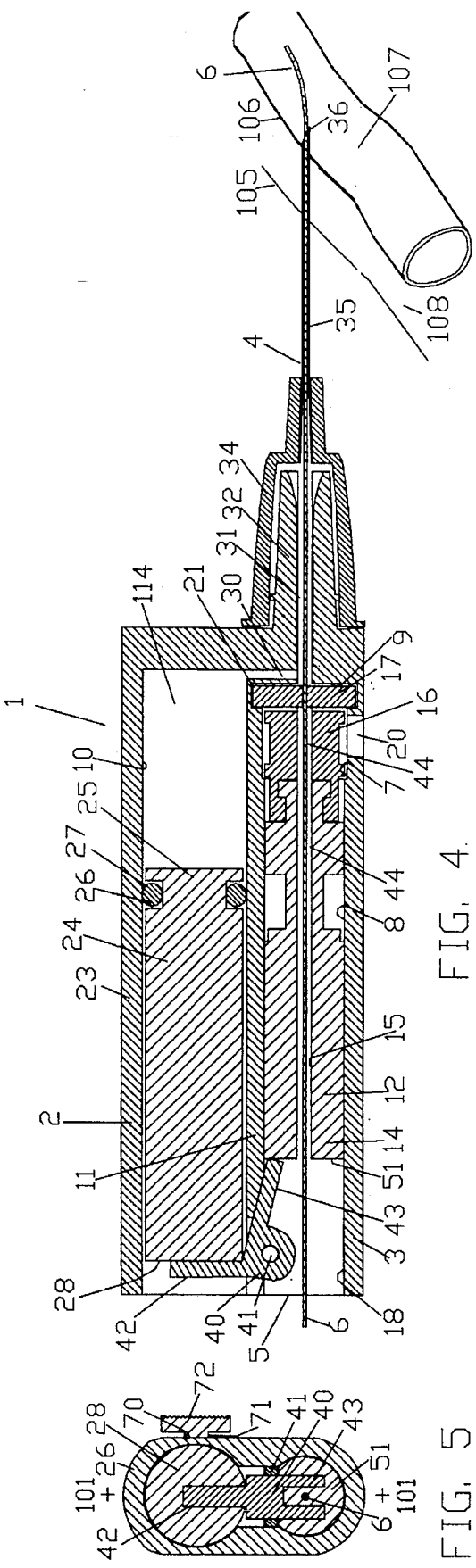

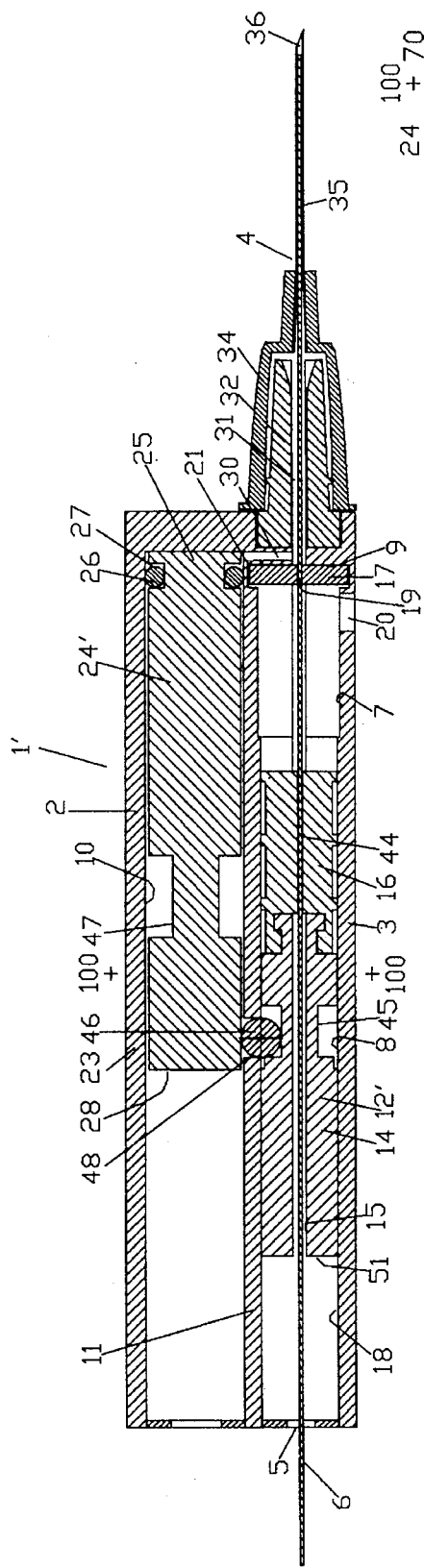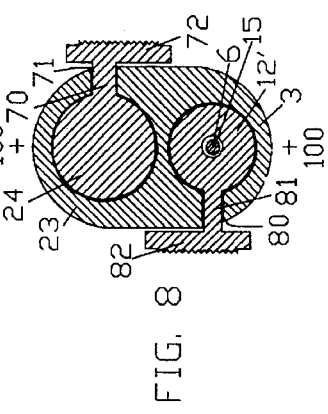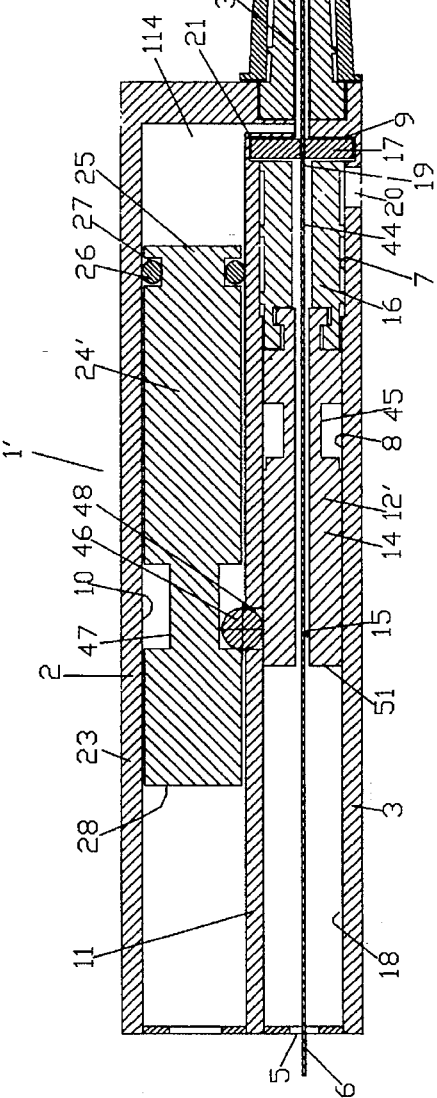

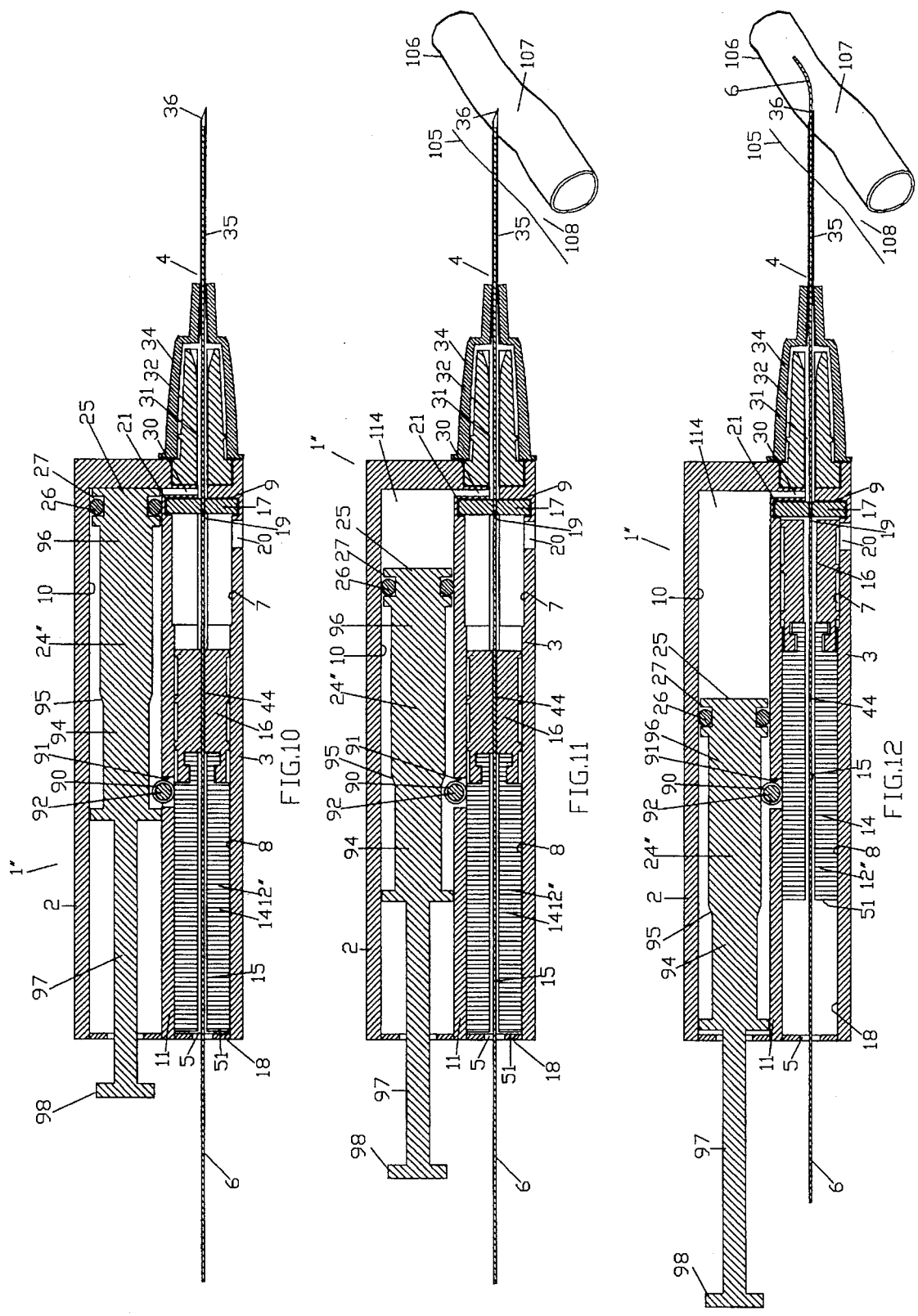

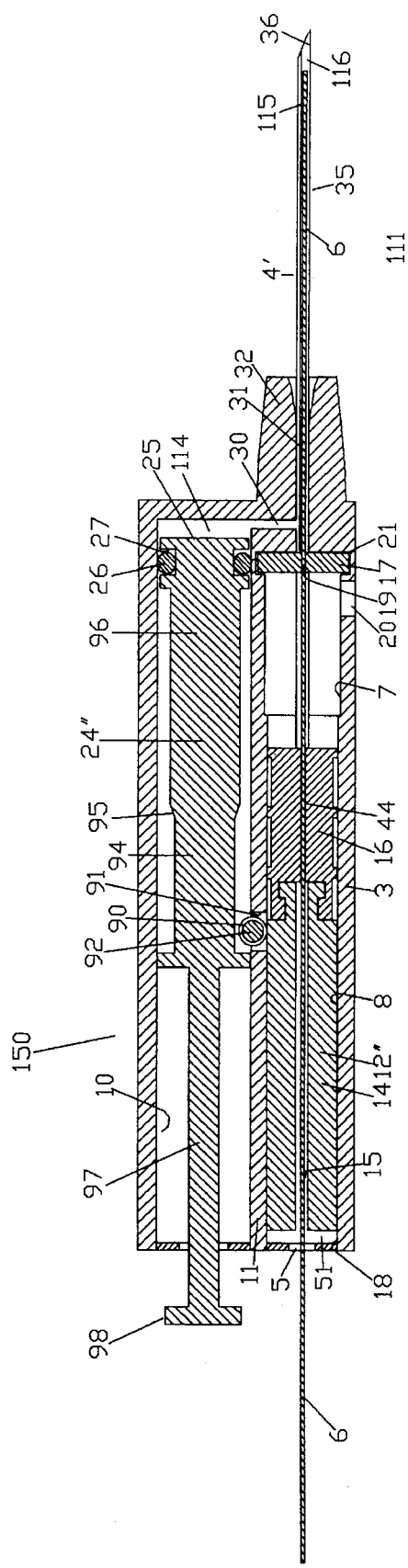
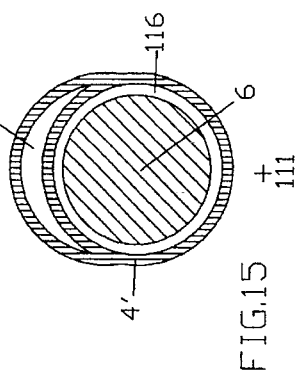
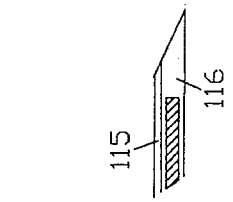
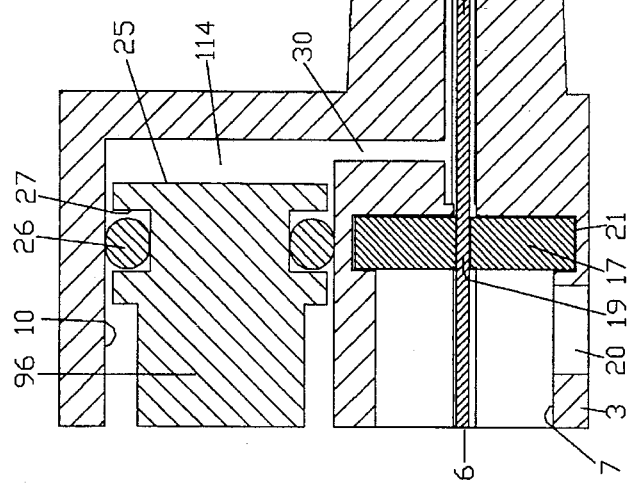

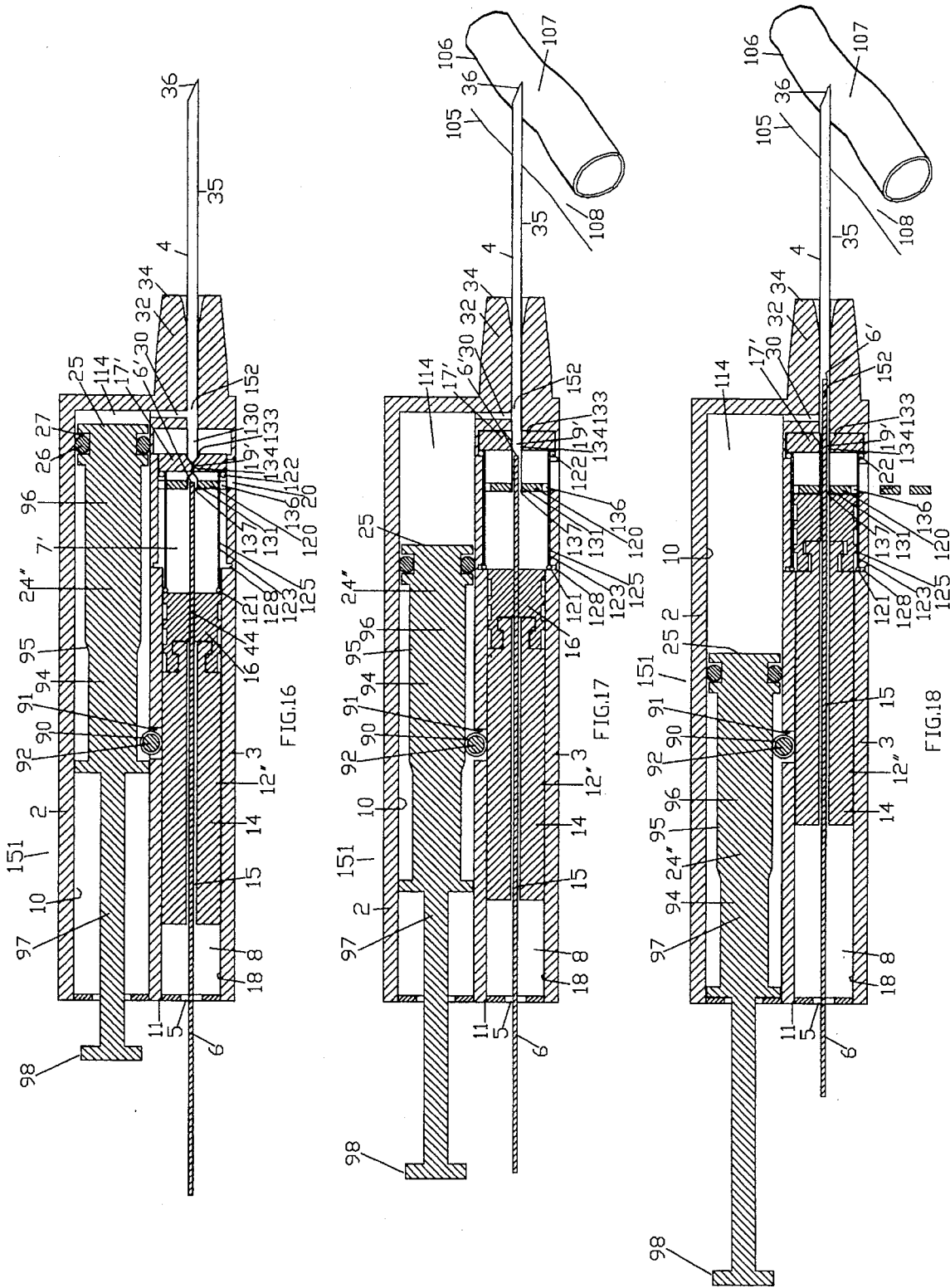

MANUAL GUIDEWIRE PLACEMENT DEVICE

BACKGROUND—FIELD OF THE INVENTION

This invention relates to guidewire placement devices for catheters of medical-surgical applications, specifically to devices concerning guidewire placement of a guidewire into the desired anatomical space such as blood vessels.

BACKGROUND—DESCRIPTION OF THE PRIOR ART

The use of guidewire in medical-surgical applications is a fairly common procedure. The procedure is based on the Seldinger technique of insertion, being Sven-Ivar Seldinger the Swedish phyisician-radiologist who first introduced the use of guidewires in medicine, a few decades ago (1953 in Sweden).

The equipment required to perform the basic technique includes:

1) a thin wall introducer hollow needle
2) a flexible wireguide or guidewire
3) a plastic preformed flexible catheter.

The procedure is carried out as follows:

The vessel is penetrated by the tip of a hollow needle, said hollow needle usually being attached to a syringe by an operator. As soon as the operator realizes that the wall of the vessel has been penetrated by the presence of blood in the syringe and that the tip of the needle is well within the blood vessel lumen, he or she detaches the syringe from the needle usually by way of unscrewing the needle hub and introduces the guidewire into the needle by feeding it through the needle hub. The operator then advances the guidewire manually by sliding it inside the hollow needle into the blood vessel. Once the guidewire is placed within the vessel up to the desired length, the operator slides the catheter over the guidewire placing the catheter well within the vessel lumen. This operation of sliding the catheter over the guide wire is accomplished, with certain types of catheters, by removing the needle and so leaving only the guidewire within the blood vessel prior to the introduction of the catheter. With other types, the needle needs not to be removed prior to the sliding of the catheter over the guide wire as the catheter is already present over the needle in concentric relation. In all situations however, the guide wire is manually advanced within the vessel lumen by the operator once the occurred penetration of the blood vessel by the hollow needle has been ascertained.

Various are the reasons for failure in this manual procedure of guide wire placement within the blood vessel lumen. The operator can fail because many factors such as inability to recognize penetration of the blood vessel wall by the needle tip, sequence delays, loss of engagement of the needle tip with the vessel not permitting advancement of the guidewire, disruption of the continuity of the blood vessel wall, patient anatomical variability, etc.

The most critical factor in successful guidewire placement is entry of the guidewire at the earliest stage of blood vessel penetration by the needle tip. Indeed, the guidewire needs to enter the blood vessel immediately upon blood vessel penetration in order to minimize the various risks of failure. The presently available technique and means of insertion lacks such an immediate entry or prompt advancement of the guidewire into the blood vessel.

To obviate the problems inherent to guidewire placement with the present techniques of insertion Zadini et al. describe an Automatic Guidewire placement device in their patent Application No. 07/999,353.

In said application an Automatic Guidewire Placement Device is described in which a guidewire is advanced by self propelling means such as a spring into the interior of a blood vessel at an early stage of blood vessel penetration by the needle tip. In a version of such a device the guidewire is automatically advanced in response to blood vessel penetration, while in another version the self propelled guidewire advancement is manually triggered by the operator upon blood vessel penetration ascertained by blood visualization. In either cases blood backflow through the needle is accelerated by vacuum means exerting suction action upon the blood trough the whole needle up the tip.

Such accelerated backflow of blood permits in the fully automatic version an almost immediate advancement of the guidewire into the interior of a blood vessel in response to blood vessel penetration, while, in the version in which the self propelled guidewire advancement is manually triggered, such accelerated backflow of blood permits a more rapid ascertainment of blood vessel penetration by the needle tip enabling the operator to trigger the self-propelled guidewire advancement at the earliest stage of blood vessel penetration by the needle tip avoiding so most frequent cause of failure.

Lynch, U.S. Pat. No. 4,917,094, describes a guidewire placement device in which a guidewire is advanced manually into a vessel lumen by friction means operated by the operator. Advancement of the guidewire is accomplished after penetration of the blood vessel by the needle. There is no connection or continuum between the two mechanisms of blood vessel penetration and guidewire advancement: no mechanism connects or mediates the two process. In the device described by Lynch guidewire placement is a multi-step process facilitated only by the presence of friction means which engages the guidewire and permit a better gripping and advancement of the guidewire compared with direct gripping and advancement by the operator hands. In Lynch patent blood vessel penetration and guide wire insertion into a blood vessel and advancement are two distinct process having no connecting mechanism.

SUMMARY OF THE INVENTION

The disadvantages of the present apparatus and methods of manual guide wire placement into the blood vessels are overcome with the present invention.

An improved manual guide wire placement device is proposed which permits rapid entry and advancement of a guidewire into a blood vessel once the blood vessel has been penetrated. In our invention the means for accelerating backflow of blood upon blood vessel penetration actuates the means for advancement of the guidewire without interruption. The two process are an operational continuum.

Accordingly, it is an object of the present invention to provide an improved guide wire placement device.

The advantage of the present invention are preferably attained by providing an improved manual guidewire placement device comprising a needle, a guidewire, manual means of accelerating backflow of blood, means for manually advancing the catheter and means for actuating said manually advancing means connecting the two processes, conferring a continuity of operation to the device, a smooth, easy one handed operation, which results in minimizing the risk of losing needle tip and guidewire engagement with the penetrated blood vessel.

With the present invention risks of needle tip disengagement with a penetrated blood vessel and by risks of blood vessel overpenetration are significantly minimized.

Actuation of means for guidewire advancement may be either achieved by release of said means for guidewire advancement, said advancing means being positioned within easy reach of the operator's hand which creates the vacuum, so that no repositioning of the vacuum creating hand nor a two hands operation is required, or may be accomplished by conversion of the manual action exerted upon said vacuum creating means into a guidewire advancing action exerted upon said means for advancing the guidewire. The above features are aimed at minimizing loss of needle tip engagement within the blood vessel and at preventing overpenetration.

DRAWING FIGURES

FIG. 2 is a cross sectional view of the catheter placement device at rest, along the longitudinal axis, prior to use.

FIG. 3 is a transverse cross sectional view of the device of FIG. 2, drawn at crosses 100.

FIG. 4 is cross sectional view of the device of FIG. 1 shown in use, after penetration of a blood vessel.

FIG. 5 is a transverse cross sectional view of the device of FIG. 2 drawn at crosses 101.

FIG. 7 is cross sectional view of the device of FIG. 6 shown prior to use.

FIG. 8 is a transverse cross sectional view of FIG. 7 drawn at crosses 100'.

FIG. 9 is a cross sectional view along the longitudinal axis of the device of FIG. 6 in use after blood vessel penetration.

FIG. 10 is across sectional view of an alternative form of the device of FIG. 1. prior to use.

FIG. 11 is cross sectional view of the device of FIG. 10 shown in use, at an early stage of blood vessel penetration.

FIG. 12 is a cross sectional view of the device of FIG. 10 after blood vessel penetration, showing advancement of the guidewire.

FIG. 13 is a cross section of another version of the device of FIG. 1 prior to use.

FIG. 14 is an enlargement of the front portion of FIG. 13.

FIG. 15 is a cross section view of the needle of FIG. 14 drawn at crosses 111.

FIG. 16 is a cross section view of another version of the device of FIG. 1, prior to use.

FIG. 17 is a cross section view of the device of FIG. 16 in use, just after blood vessel penetration, showing initial advancement of the guidewire within the needle lumen.

FIG. 18 is a cross section view of the device of FIG. 16 showing further advancement of the guidewire within the needle lumen after blood vessel penetration.

DETAILED DESCRIPTION OF THE INVENTION

Figure 1:
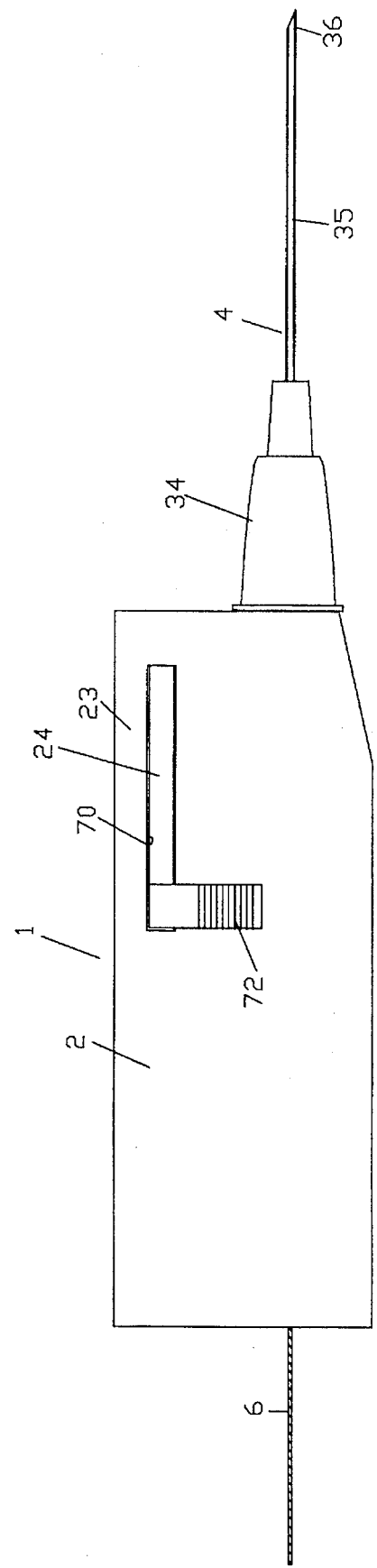
FIG. 1 is side view of the manual guidewire placement device.

A typical embodiment of the Manual Guidewire Placement is illustrated in FIG. 1 to 5. FIG. 1 is a side view of the device, generally indicated at 1, prior to use. The device is composed of three main parts: a housing 2, a needle 4 and a guidewire 6.

FIG. 2 is a cross-sectional view of the device of FIG. 1. Housing 2 is composed of two parallel chambers of generally cylindrical shape: guidewire chamber 8 and vacuum chamber or vacuum means 10, separated longitudinally by divider wall 11.

Guidewire chamber 8 delimited laterally by side wall 3 has a posterior segment 18 and an anterior segment 7 of larger diameter and shorter length than posterior segment 18. Guidewire chamber 8 is open posteriorly via opening 5 while 9 is its anterior wall. Within guidewire chamber 8 is slideably mounted guidewire piston 12. Guidewire piston 12 is composed of a posterior segment 14 and anterior segment or guidewire introducer 16 made of resilient compressible/expandable material such a rubber or could be designed as a mandrin or as a chuck. Posterior segment 14 of guidewire piston 12 has at its center axial tract 15 for guidewire 6 which is mounted in a slideable fashion within axial tract 15, while, as shown in FIG. 2, in position of rest prior to use, guidewire introducer 16, compressed within posterior narrower chamber 18, is tightened in a gripping fashion around guidewire 6 mounted within passageway 44 of guidewire introducer 16. Sealing Member Or Means 17 seats hermetically sealed on annular recess 21 in proximity or contact with anterior wall 9 of guidewire chamber 8 providing sealing around guidewire 6 within passageway 19 located at the center of sealing member or means 17, guidewire 6 remaining slideable along passageway 19 of sealing member or means 17. For the purpose of sealing in certain types of guidewires, the space between the core-wire and the spires can be filled with sealable material such as plastic or metal. The outer surface of the guidewire can be leveled between the spires with the same material to obtain a smooth cylindrical surface. Window 20 is located in antero-inferior aspect of anterior segment 7 of guidewire chamber 8 to permit the exit of air from anterior segment 7 of chamber 8 during the operation, as it will be described below in the description of the operation.

Within vacuum chamber 10 of general cylindrical shape, delimited laterally by side wall 23, is mounted in slideable fashion piston 24. Piston head 25 of piston 24 has sealing O-ring 26 seating on annular recess 27, providing sealing between piston 24 and lateral wall 23 of vacuum chamber 10. Piston 24 has a posterior face 28. Space 114 is the space within chamber 10 in front of piston head 25.

As better seen in FIG. 1 and 3, side wall 23 of vacuum chamber 10 is also formed with lateral slit 70 for arm 71 of handle 72 of vacuum piston 24, said handle 72 being connected via said arm 71 to vacuum piston 24. Slit 70 permits the sliding of vacuum piston 24 by the operator acting upon said handle 72 as it will be explained below in the description of the operation.

As better shown in Fig.4 space 114 of vacuum chamber 10 communicates via conduit 30 within anterior wall 9 of guidewire chamber 8 with passageway 31 in nozzle 32 of housing 2, said nozzle 32 protruding forwardly from the anterior lower aspect of housing 2. As shown in FIG. 2 and 5, lever 40 is positioned posteriorly mounted within slit 50 of divider wall 11 via pin 41. Lever 40 is composed of upper arm 42 and two parallel lower arms 43 connected to center of lever 40 in inverted U shape fashion.

In position of rest prior to use lower arms of lever 40 are in contact with posterior face 51 of guidewire piston 12.

Needle 4 is composed of needle shaft 35, needle hub 34 which seats circumferentially on nozzle 32 of housing 2, and needle tip 36. Guidewire 6 is slideably mounted with the device in position of rest prior to use from front to back within hollow needle 4, passageway 31 of nozzle 32, passageway 19 of sealing member or means 17, passageway 44 of guidewire introducer 16, axial tract 15 of guidewire piston 12, exiting posteriorly from guidewire piston posterior end 51, then passing between lower arms 43 of lever 40, and finally exiting from opening 5 of guidewire piston chamber 8 to continue posteriorly outside of device 1.

Description of the operation

The device is operated as follows: the operator with the device in his or her hands will penetrate with needle tip 36 of needle 4 the skin 105, FIG. 4, of a patient in an area overlying the central vessel or body cavity where the guidewire is intended to be placed. Please refer to FIG. 4 for the anatomy of the body area, 105 being the skin, 108 the subcutaneous tissue, 106 the wall of the blood vessel, and 107 the blood vessel.

As soon as needle tip is well under the skin, in subcutaneous tissue 108, the operator will act upon handle 72 of vacuum piston 24 by sliding it posteriorly. He or she could use any finger of the operating hand to slide posteriorly vacuum piston 24 by acting on handle 72.

Posterior displacement of piston 24 will create a vacuum in front of piston head 25 in space 114. However, posterior displacement of piston 25 will be only of a small amount, due to the sealing of needle tip 36 caused by the patient subcutaneous tissue 108, as the operator senses sufficient resistance opposing the further posterior displacement of piston 24, such resistance being caused by the vacuum being created in space 114, in front of piston head 25 of piston 24. As shown in FIG. 4, as soon as needle tip 36 will penetrate the desired blood vessel 107, such as for instance the femoral vein or artery, by perforating its wall 106, blood backflow will occur in an accelerated fashion into vacuum chamber 10 in front of piston head 25, blood rushing into it space 114, passing trough conduit 30. The backflow of blood will cause a near sudden vanishing or dropping of the vacuum pressure created in the prior stage in front of piston head 25 of piston 24 within vacuum chamber 10. Such vanishing of the vacuum or decrease of the vacuum pressure will not retain any longer piston 24 in the advanced position above described, allowing so full posterior displacement of piston 24 by the operator acting on handle 72. Posterior displacement of piston 24 will cause lever 40 to be tilted backwardly by the posterior face 28 of piston 24 acting upon upper arm 42 of lever 40. Arms 43 of lever 40 will be consequently tilted anteriorly causing consequently advancement of guidewire piston 12, said lower arms 43 of lever 40 acting upon posterior face 51 of guidewire piston 12. Guidewire introducer or anterior guidewire piston segment 16, being advanced with piston 12, will carry forward guidewire 6 due to the gripping action of guidewire introducer 16, tightened around guidewire 6 along passageway 44 of guidewire introducer 16. As soon as guidewire introducer 16 will enter anterior segment 7 of guidewire chamber 8, guidewire introducer 16, made, as above described, of resilient material, will be able to expand in anterior segment 7 of guidewire chamber 8, being anterior segment 7 of larger diameter than guidewire chamber posterior segment 14. During advancement of guidewire introducer 16 air will be expelled trough window 20 avoiding so any opposing resistance to the advancement of guidewire introducer 16 and avoiding introduction of said air into needle 4 and ultimately into blood vessel 107. Guidewire introducer 16, once fully advanced into anterior segment chamber 7, will release completely the grip on guidewire 6, free now to be slided in both directions, forwardly and backwardly by the operator's hands along and within hollow needle 4, passageway 31 of housing nozzle 32, passageway 19 of sealing member or means 17, passageway 44 of guidewire introducer 16, axial tract 15 of guidewire piston 12.

Once the guidewire's tip is engaged in the blood vessel, the insertion of the guidewire is secured. Further advancement of the guidewire can be carried out by the operator either by first extracting the device out of the guidewire, and then by manually advancing the guidewire fully into position, or the operator may by first fully advance the guidewire through the device into the blood vessel, and then extracting the device. In this second option, after the critical initial advancement carried out by introducer 16 which will result with engagement of the tip of the guidewire into the blood vessel, and therefore with a secured guidewire insertion, partial or full advancement of the guidewire 6 into the blood vessel 107 can be achieved, besides manually as described, also by resilient means which can propel guidewire 6 further into the blood vessel.

Figure 6:
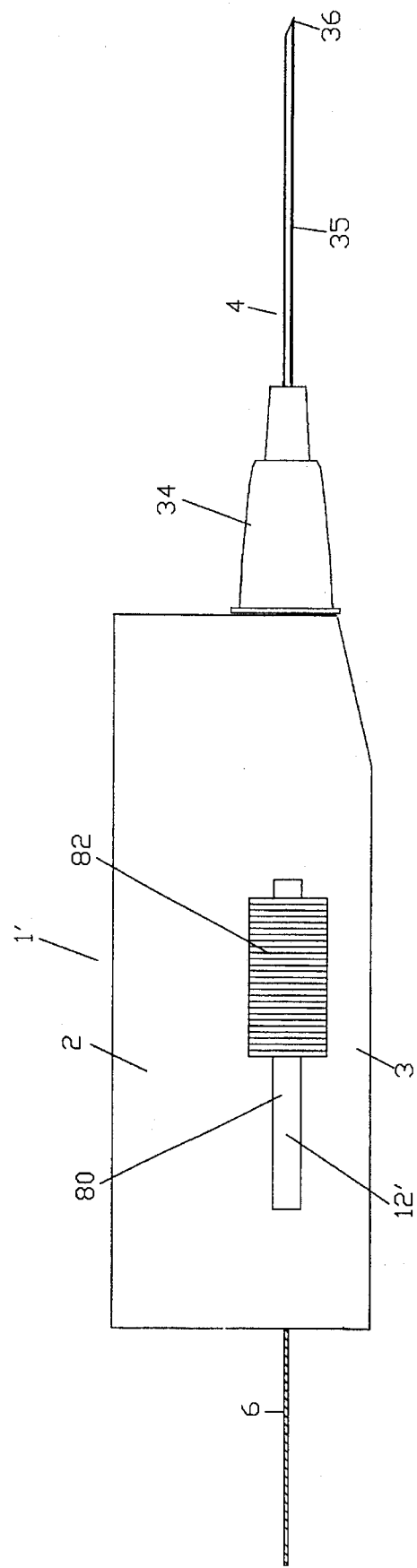
FIG. 6 is a side view of another version of the device of FIG. 1 to 5.
Figure 19:
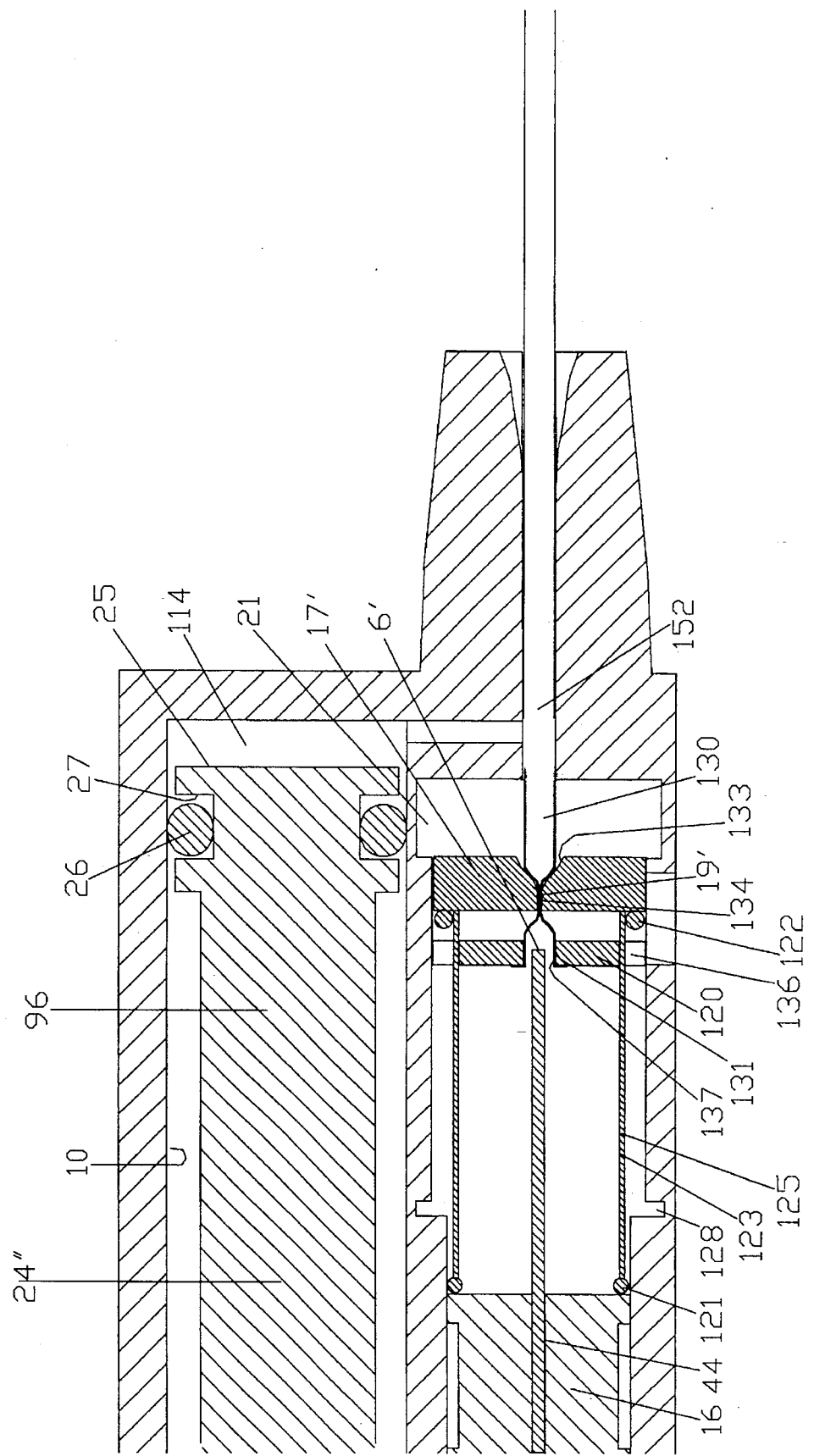
FIG. 19 is a n enlarged cross section view of front portion of FIG. 16.

FIGS. 6 to 9 show an alternative form of the device described in FIGS. 1 to 5, generally indicated at 1'. FIG. 6 is a side view of the device, precisely the opposite side of the one described in FIG. 1. The device is basically the same as the one described in FIGS. 1 to 5 except for few differences outlined below. Lever 40 is no longer present. Both pistons, vacuum piston 24' and guidewire piston 12' have respectively annular recess 47 and 45 for ball member 46, as it will be described in the description of the operation. Window 48 is formed in divider wall 11 between intermediate vacuum chamber 10 and guidewire chamber 8 to house ball member 46.

Beside vacuum piston 24', also guidewire piston 12' has an handle apparatus as shown in FIGS. 6 and 8.

The handle apparatus of vacuum piston 24' is exactly the same as the one described for the device of FIGS. 1 to 5.

Handle apparatus of guidewire piston 12' is shown in FIGS. 6 and 8, FIG. 8 being a cross section of the device 1' of FIG. 6 drawn through plane at crosses 100. Side wall 3 of guidewire piston chamber 8 has a lateral slit 80 for arm 81 of side piston handle 82 connected via said arm 81 to guidewire piston 12'. Slit 80 permits the sliding of the piston 12' by the operator acting upon said side piston handle 82 as it will be described in the operation.

Vacuum piston 24' may also be designed as a piston plunger such as a syringe plunger wherein the operator withdraws the piston by pulling back the plunger handle. However, the above described piston version with side handle 72 is preferable, being designed to render manual withdrawal of piston 24' via displacement of side handle 72 an easy and convenient operation for the operator's hand holding the device, averting the use of two hands, which is likely to occur in the mentioned version with the plunger.

As shown in FIG. 7, with device 1' in position of rest, prior to use, ball member 46 is shown as being engaged in window 48 of divider wall 11, seating inferiorly on annular recess 45 of guidewire piston 12' locking said guidewire piston 12'.

In one embodiment, side wall 23 of vacuum chamber 10 should permit visualization of the interior of the chamber 10, for instance by being made of transparent material.

Description of the operation

The device is operated as the previously described device except that once blood vessel penetration is ascertained by the operator by visualization of blood within vacuum chamber 10 in front of piston head 25 of piston 24' or such blood vessel penetration is sensed by the fall of resistance to the continuous withdrawing force applied by the operator upon said piston 24' via piston handle 72, the operator will further displace piston 24' acting on handle 72. Simultaneously the operator will displace anteriorly piston 12' via acting on handle 82 with another finger of the Same hand in a way that, while piston 24' is displaced posteriorly simultaneously guidewire piston 12' is being displaced anteriorly.

Such anterior displacement of guidewire piston 12' is permitted as a result of the release/exit of locking ball 46 from recess 45 of guidewire piston 12' through window 48, occurring with the withdrawal of vacuum piston 24'. As matter of fact, ball 46 will be ejected, forced out from recess 45 of piston 12' by the advancement of piston 12', due to the fact the equator of ball 46 is above the lower edge of window 48. Ejection of ball 46 occurs upon alignment of both recesses 47 of piston 24' and 45 of piston 12'. Ejection of ball 46 can be facilitated by a slanting of the posterior edge of recess 45.

Anterior manual displacement of guidewire piston 12' will result in engagement of advancement of guidewire 6 into blood vessel 107. The remainder of the operation is exactly the same as the one described for the device in FIGS. 1 to 5.

FIGS. 10 to 12 show an alternate form of the device 1 of FIGS. 1 to 5. In this form, generally indicated at 1", propelling of guidewire 6 is accomplished via the interposition of friction roll 90 positioned between vacuum piston 24" and guidewire piston 12". As shown in FIG. 10 the device is basically the same as the one described in FIGS. 7 to 10 except that ball 46, recesses 48 and 47 respectively of vacuum piston 24' and guidewire piston 12", window 48, handle apparatus of guidewire piston 12', including slit 80, piston handle 82 with its arm 81 are no longer present. Vacuum piston 24" can be exactly the same as the ones described for the device of FIGS. 1 to 5 or 6 to 9 with the same handle apparatus for posterior displacement or can be devoid of an handle apparatus being instead designed as a piston plunger as in FIG. 10, being 98 the T bar and 97 the handle. Friction roll 90 is positioned between guidewire piston 12" and vacuum piston 24", friction roll 90 being mounted in seating 91 of divider wall 11 via center pin 92. Friction roll 90 can be substituted by a toothed wheel or gear engaging corresponding toothed racks in both vacuum piston 24' and guidewire piston 12". Posterior piston segment 94 of vacuum piston 24' is of smaller diameter than proximal segment 96 in order to delay purposely friction engagement of vacuum piston 24' with roll 90, up to piston slant 95 as it will be evident from the description of the operation outlined below.

Description of the operation

The device is operated as the previously described devices. In this version piston 24' displaced posteriorly manually by the operator acting upon handle 97 will propel forward guidewire piston 12", resulting in advancement of guidewire 6 into a blood vessel.

After skin 105 is penetrates by needle tip 36, the operator pulls backward piston 24" creating a vacuum in front of piston head 25 in space 114. Posterior displacement of piston 24" will be only of a fraction of amount due to the sealing of needle tip 36 caused by the patient subcutaneous tissue 108, as the operator senses sufficient resistance opposing the further posterior displacement of piston 24", such resistance being caused by the vacuum being created in space 114 in front of piston head 25 of piston 24". As shown in FIG. 11, as soon as needle tip 36 will penetrate the desired blood vessel 107, such as for instance the femoral vein or artery, by perforating its wall 106, blood backflow will occur in an accelerated fashion into vacuum chamber 10 in front of piston head 25, blood rushing into it space 114, passing trough conduit 30. The backflow of blood will cause a near sudden vanishing or dropping of the vacuum pressure created in the prior stage in front of piston head 25 of piston 24" within vacuum chamber 10. Such a vanishing of the vacuum or decrease of the vacuum pressure will not retain any longer piston 24" in the advanced position above described, allowing further posterior displacement of piston 24". Engagement of roll 90 by slant 95 of piston 24" will initiate forward propelling of piston 12". As shown in FIG. 12, forward propelling of guidewire piston 12" will be accomplished by the rotation of friction roll 90 caused by the manual backward displacement of posterior piston segment 94 of piston 24". While vacuum piston 24' is manually displaced posteriorly by the operator, guidewire piston 12" will be displaced in the opposite direction i.e. forwardly, resulting, as above described, in advancement of guidewire 6 into blood vessel 107.

FIGS. 13 to 15 describe another version, generally indicated at 150, of device 1 of FIGS. 1 to 5. This device is very similar to the device 1' of FIGS. 10 to 12, except that, in this version, aspiration of blood from the blood vessel does not occur via lumen 116 which houses guidewire 6, but occurs via an additional lumen formed in needle 4'. As shown in FIGS. 13 and 14, and more clearly in 15, which is a transversal cross section of needle 4', needle 4' is divided in at least two parallel compartments. Lower compartment 116 houses the guidewire 6 while upper compartment 115 is empty and its function is to aspirate the blood when piston 24" is displaced posteriorly by the operator as per the device of FIGS. 10 to 12. Indeed, compartment for blood aspiration in needle 4' can either be a single lumen or a multiple lumen.

Description of the operation

In use, device 150 is operated exactly as device 1" of FIGS. 10 to 12. Blood however will reach vacuum chamber 10, specifically space 114 in front of piston 24", via upper compartment 115 of needle 4'. No aspiration of blood will occur through lower compartment 116 of needle 4" as there is no communication between needle lower compartment 116 and vacuum chamber 10, as conduit 30 opens in upper compartment 115 of needle 4' as better shown in FIG. 14.

FIGS. 16 to 19 describe another version of device 1 of FIGS. 1 to 5. This device, generally indicated at 151 is very similar to device 1" of FIGS. 10 to 12, except that, as shown in FIG. 6 and, better, in FIG. 19, in this version tip 6' of guidewire 6 is positioned, with the device in position of rest prior to use, posteriorly to needle 4, not engaging proximal end 152 of needle 4.

As shown in FIG. 16 device 151 is very similar to the device of FIGS. 10 to 12 except for the differences outlined below. The differences between the devices are all confined in guidewire piston chamber 8 precisely in its anterior segment 7'. Anterior segment chamber 7' has annular recess 128 on its very proximal segment. Sealing Member Or Means 17' is not positioned adjacent to anterior wall 9 of guidewire piston chamber 8 as for the device 1" of FIGS. 10 to 12, but is positioned posteriorly, fully contained within chamber 7' by the anterior edge of it, just proximal to annular recess 21 of sealing member or means 17'. Sealing Member Or Means 17' is made of resilient compressible material able to rapidly expand. Passageway 19' of sealing member or means 17' is composed of two segments, anterior expanded segment 133, funnel shaped and posterior narrow segment 134, both engaging pipe 130 as it will be described below.

Anterior piston or guidewire introducer 16 is in contact with cylindrical expandable frame or interface member 125 which is composed of a posterior ring 121 and of anterior ring 122 joined together by connecting rods 123. Rings 121 and 122 are made of expandable resilient material such as plastic or steel. Circular diaphragm 120 is interposed and firmly positioned within chamber 7', between guidewire introducer 16 and sealing member or means 17'. Collapsible pipe 130 is positioned at the center of diaphragm 120 and of sealing member or means 17', respectively within passageway 131 of diaphragm 120 and passageway 19' of sealing member or means 17', bridging diaphragm 120 and sealing member or means 17'. With the device in position of rest, collapsible pipe 130, expanded within passageway 13 1 of diaphragm 120, continues anteriorly constricted within posterior narrow segment 134 of passageway 19' of sealing member or means 17', and expands within funnel shaped anterior expanded segment 133 of same passageway 19'. Expanded proximal segment 137 of pipe 130 contained within passageway 131 of diaphragm 120 houses distal end 6' of guidewire 6. Circular diaphragm 120 has also slits 136 to permit the expansion of rods 123 as it will be understood from the description of the operation.

Description of the operation

The device 151 is operated as device 1" of FIGS. 10 to 12. As soon as needle 136 will penetrate blood vessel 107, blood will be aspirated via needle 4 into space 114 in front of piston head 25 of vacuum piston 24", sealing being secured by compressed sealing member or means 17' constrained and tightened around pipe 130 within chamber 7'. As shown in FIG. 17, as soon as piston 24" is displaced posteriorly by the operator upon blood vessel penetration by needle tip 36, such a displacement will cause advancement of guidewire piston 12" by engagement and rotation of friction roll or gear 90.

Advancement of guidewire introducer 16 with guidewire piston 12" will initiate the advancement oil interface member 125 which on its turn will displace anteriorly sealing member or means 17' which will then be allowed to expand in annular recess 21' of sealing member 17'. Passageway 19'of sealing member 17' will follow expansion of sealing member or means 17' permitting the expansion also of collapsible pipe 130, said pipe no longer being constrained within narrow segment 134 of passageway 19', as shown in FIG. 17. Upon completion of entry of sealing member 17' into annular recess 21', rings 121 will be aligned with correspondent annular recess 128, while ring 122 will be aligned with the front portion of annular recess 21', said front portion being left vacant by the sealing member entered in annular recess 21'. The alignment of expandable rings 121 and 122 with correspondent annular recesses will permit expansion of said rings 121 and 122, and with expansion of rings 121 and 122, also rods 123 will be radially and outwardly displaced. Expansion of expandable interface member 125 will allow further advancement of guidewire introducer 16, which will slide inside expanded interface member 125 to further advance guidewire 6 into needle 4 into a more advanced position.

As shown in FIG. 18, tip 6' of guidewire 6, carried forward by guidewire introducer 16 will be able to advance through pipe 130 and enter the lumen of needle 4 in its proximal end 4'. advancement of guidewire introducer 16 by rotation of friction roll or gear 90 will stop upon contact of guidewire introducer 16 with diaphragm 120.

Guidewire 6 will then be advanced manually by the operator by sliding it forwardly within the lumen of needle 4 up to entering blood vessel 107.

Once guidewire 6 is engaged with the blood vessel 107 the remainder of the operations is exactly as the one described for device 1" of FIGS. 10 to 12.

Obviously, numerous other variations and modifications can be made without departing from the spirit of the present invention. Therefore, it should be clearly understood that the forms of the present invention described above and shown in the figures of the accompanying drawing are illustrative only and are not intended to limit the scope of the present invention.

What we claim is:

1. A guidewire placement device for insertion of a guidewire into the interior of a blood vessel comprising:
    a hollow needle, for the passage of (said) a guidewire, said needle having a tip,
    a vacuum means for enclosure of a vacuum pressure, said hollow needle being in flow communication with said vacuum means,
    means for manually creating said vacuum pressure within said vacuum means,
    means for manually advancing said guidewire, said means for manually advancing being actuable by said means for manually creating said vacuum.

2. The device of claim 1 wherein said means for manually creating said vacuum actuates said means for manually advancing said guidewire by releasing locking means releasably retaining said guidewire for manual advancement.

3. The device of claim 1 wherein said means for manually creating vacuum actuates said means for manually advancing said guidewire by a conversion of a manual action exerted upon said vacuum creating means into a guidewire advancing action upon said means for advancing said guidewire.

4. The device of claim 1 wherein said means for manually creating said vacuum is a manually displaceable piston means.

5. The device of claim 4 wherein said piston means has a handle for said manual displacement.

6. The device of claim 3 wherein said conversion of said manual action exerted upon said vacuum creating means into a guidewire advancing action upon said means for advancing said guidewire is actuable by engaging means comprising means for engagement of said manual vacuum creating means with said means for advancing said guidewire.

7. The device of claim 6, wherein said means for engagement of said manual vacuum creating means with said means for advancing said guidewire comprises means converting a manual withdrawal movement exerted upon said vacuum creating means into a movement in opposite direction of said guidewire advancing means.

8. The device of claim 6 wherein said engaging means comprises a lever means adapted to transfer said manual action being exerted upon said manual vacuum creating means to said means for advancement of said guidewire.

9. The device of claim 6 wherein said engaging means comprises a toothed wheel means adapted to transfer said manual action exerted upon said manual vacuum creating means to said means for advancement of said guidewire.

10. The device of claim 6 wherein said engaging means comprises a rotating means engaging, by friction, said manual vacuum creating means with said means for advancement of said guidewire.

11. The device of claim 6 wherein said engaging means comprises a coupling means connecting said manual vacuum creating means with said means for advancement of said guidewire to cause advancement of said guidewire to an advanced position upon manual action exerted on said vacuum creating means.

12. The guidewire placement device of claim 1 further comprising:

means for sensing penetration of a blood vessel by said hollow needle.

13. The guidewire placement device of claim 1 wherein:

said vacuum means is provided with a passageway to allow entry of said guidewire into said vacuum means, said passageway being closed by sealing means to allow enclosure of said vacuum pressure within said vacuum means, said vacuum pressure being formed in said vacuum means upon tissues sealing of the needle tip occurring upon penetration of said needle tip into tissues overlaying said blood vessel, said vacuum pressure accelerating a backflow of blood toward said vacuum means upon blood vessel penetration by said needle tip, said passageway being opened to allow entry of said guidewire, said guidewire being manually advanceable by said means for manually advancing said guidewire, said advancing means being actuable by said means for manually creating said vacuum, said guidewire being advanceable through said passageway and through said needle into said blood vessel upon blood vessel penetration.

14. A guidewire placement device for insertion of a guidewire into the interior of a blood vessel, comprising:

a housing including a vacuum means for enclosure of a vacuum pressure, a hollow needle in flow communication with said vacuum means, said needle having a tip, a guidewire entering said vacuum means, and a sealing means, said sealing means sealingly engaging to the housing the guidewire entering said vacuum means, means for forming a vacuum pressure in said vacuum means upon tissues sealing of the needle tip occurring upon penetration of said needle tip into tissues overlaying said blood vessel, said vacuum pressure accelerating a backflow of blood toward said vacuum means upon blood vessel penetration of said needle tip, said guidewire being advanceable through said needle into said blood vessel upon blood vessel penetration by manual means of advancement, said means for manually advancing the guidewire being actuable by said means for forming said vacuum pressure in said vacuum means.

15. The guidewire placement device of claim 14, wherein:

said sealing means is adaptable to a configuration of said guidewire to secure sealing of said guidewire to said sealing means.

16. The guidewire placement device of claim 14, wherein:

said guidewire having spires and at least one core wire, has at least one modified segment adaptable to said sealing means, wherein said modified segment of said guidewire has an even surface leveling up depressions between crests of said spires belonging to said segment of said guidewire, and has a sealed space between said spires and said core-wire belonging to said segment of of said guidewire, said modified guidewire segment securing sealing of said guidewire to said sealing means.

17. A guidewire placement device for insertion of a guidewire into the interior of a blood vessel, comprising:

a housing including a vacuum means for enclosure of a vacuum pressure, a multiple lumen needle, said needle having a tip, one lumen to allow passage of a guidewire, and at least another lumen being in flow communication with said vacuum means, means for forming a vacuum pressure in said vacuum means upon tissues sealing of said lumen in flow communication with said vacuum means, said tissues sealing of said lumen occurring upon penetration of said needle tip into tissues overlaying said blood vessel, said vacuum pressure accelerating a backflow of blood toward said vacuum means upon blood vessel penetration of said needle tip, said guidewire being advanceable along its lumen within said needle into said blood vessel upon blood vessel penetration, by means of advancement, said means for advancing the guidewire being actuable by said means for forming said vacuum pressure in said housing.

18. A guidewire placement device for insertion of a guidewire into the interior of a blood vessel, comprising:

(a) a hollow needle, (b) a housing connected to said needle, said housing comprising means accelerating a backflow of blood toward said housing upon blood vessel penetration by said needle, (c) a guidewire slideable within said hollow needle, and (d) means for manually advancing said guidewire through said needle into said blood vessel upon blood vessel penetration, said means for manually advancing said guidewire being actuable by said means accelerating the backflow of blood toward the housing upon blood vessel penetration.

* * * * *